US006584826B2

(12) United States Patent
Stephenson et al.

(10) Patent No.: US 6,584,826 B2
(45) Date of Patent: Jul. 1, 2003

(54) GAS TESTER

(76) Inventors: William B. Stephenson, 53 W. Bay Heights Rd., Unit 205, Eaglewood, FL (US) 34223; Craig W. Stephenson, 21749 Arrowhead, St. Clair Shores, MI (US) 48082

( * ) Notice: Subject to any disclaimer, the term of this patent is extended or adjusted under 35 U.S.C. 154(b) by 92 days.

(21) Appl. No.: 09/923,165

(22) Filed: Aug. 6, 2001

(65) Prior Publication Data
US 2002/0029607 A1 Mar. 14, 2002

Related U.S. Application Data
(60) Provisional application No. 60/223,518, filed on Aug. 7, 2000.

(51) Int. Cl.[7] ............................................. G01N 31/22
(52) U.S. Cl. ......................... 73/31.03; 73/23.2; 422/87
(58) Field of Search ............................... 73/23.2, 31.03, 73/31.05, 23.31, 1.01, 1.57; 422/87

(56) References Cited
U.S. PATENT DOCUMENTS

| | | | | |
|---|---|---|---|---|
| 3,661,009 A | * | 5/1972 | Leonard et al. | 73/31.03 X |
| 4,404,850 A | * | 9/1983 | Hickmann | 73/161 |
| 4,459,266 A | * | 7/1984 | Lamoreaux | 422/86 |
| 4,784,959 A | * | 11/1988 | Wegrzyn | 73/52 X |
| 4,859,419 A | * | 8/1989 | Marks et al. | 422/56 |
| 5,571,948 A | * | 11/1996 | Kaplan et al. | 73/31.03 X |
| 6,435,003 B1 | * | 8/2002 | Warburton | 73/23.2 |
| 2002/0100311 A1 | * | 8/2002 | Eddy, Jr. et al. | 73/1.01 X |

FOREIGN PATENT DOCUMENTS

DE 29621962 * 2/1997 .......... G01N/31/22

\* cited by examiner

Primary Examiner—Thomas P. Noland
(74) Attorney, Agent, or Firm—Gifford, Krass, Groh, Sprinkle, Anderson & Citkowski, P.C.

(57) ABSTRACT

Apparatus for testing the quality of air in sources of compressed air in which a housing forms an elongated bore closed at one end by an elastomeric bag or balloon and at the other end by a check valve to form a chamber to hold a test strip which is chemically treated to change color or characteristics when air contaminants are present. The air to be tested is introduced through the valve to inflate the balloon and maintain the test strip under air pressure where it can be viewed through a transparent portion of the housing.

14 Claims, 2 Drawing Sheets

GAS TESTER

This application claims the benefit of Provisional Patent Application Ser. No. 60/223,518 filed Aug. 7, 2000.

FIELD OF THE INVENTION

This invention relates to testing equipment for gases and more particularly equipment for testing for the presence of carbon monoxide in compressed air used by underwater divers.

BACKGROUND OF THE INVENTION

The presence of carbon monoxide in compressed air used in association with underwater breathing apparatus can be extremely poisonous and fatal. Divers typically use extreme precaution with respect to the safety aspects of scuba diving equipment, but unfortunately there is no known economical means of testing for the presence of carbon monoxide in the breathing apparatus.

SUMMARY OF THE INVENTION

It is an objection of the invention to provide an economical testing apparatus for testing for the presence of carbon monoxide or other contaminants in compressed air tanks used by scuba divers.

It is a further object of the invention to provide testing apparatus for compressed air used in association with underwater breathing apparatus, which is easily operated and produces rapid results.

Another object of the invention is to provide testing apparatus which is easily portable and can be used without the need for additional tools to install it in the compressed air system to be tested.

The object of the invention is attained by an apparatus having a hand-held head member detachably connected to a tubular member extending therefrom so that the head member forms a continuous bore closed at one end by an elastomeric bag or balloon and at the other end by a check valve. The bore holds a disposable test strip which responds to constituents in air to change color and which can be viewed through transparent portions of the tubular member. The apparatus is held against the outlet of a source of air to be tested to inflate the balloon and to maintain the test strip in an atmosphere of compressive air from the source to be tested after the apparatus is separated from the source.

These and other objects of the invention will become apparent from the following description and from the drawings.

DETAILED DESCRIPTION

Figure 1:
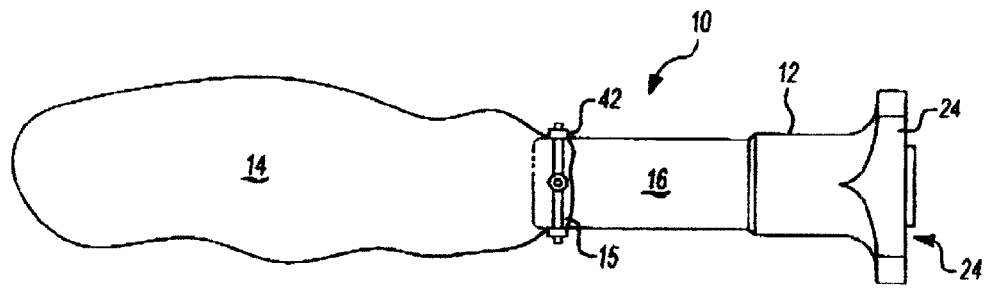
FIG. 1 is an elevational view for testing apparatus embodying the invention.
Figure 2:
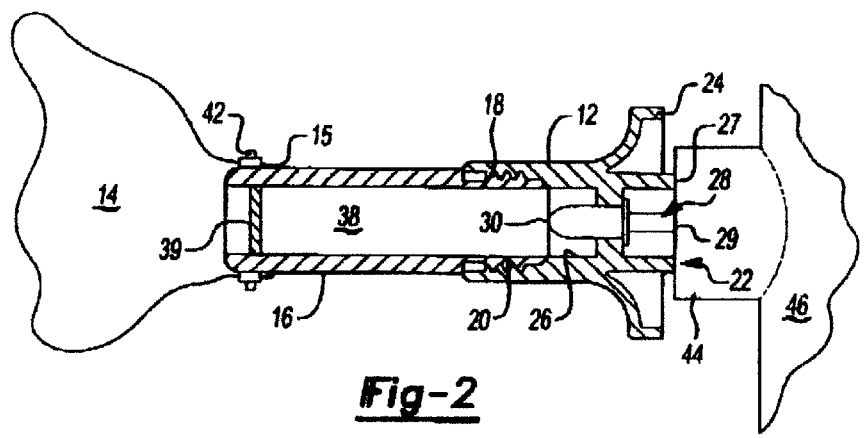
FIG. 2 is a cross-sectional view of a portion of the testing apparatus seen in FIG. 1 in association with a source of air shown partially.
Figure 3:
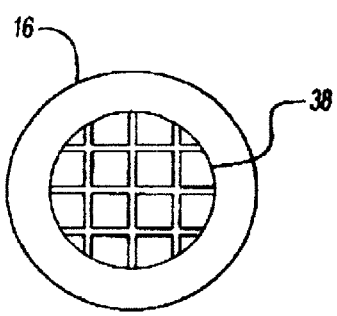
FIG. 3 is a left end view of the structure in FIG. 2.
Figure 4:
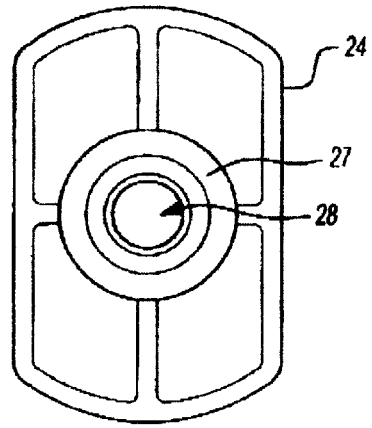
FIG. 4 is a view from the right end of the structure seen in FIG. 2.
Figure 5:
FIG. 5 is a view of the test strip used with the test apparatus seen in FIGS. 1 and 2.

The testing apparatus embodying the invention is designated generally at 10 and includes a housing member 12, one end of which is provided with an expandable member in the form of an elastomeric balloon 14 to receive air or other gas to be tested. The housing 12 is generally tubular and includes an elongated tubular element 16 having one end to receive a neck 15 of the balloon 14 and the other end having external threads at 18 to receive complementary internal threads 20 in a head member 22. The head member 22 also is generally tubular and has a flange 23 extending radially from diametrically opposed sides of the head member 22 to provide a handle for grasping the test apparatus 10.

The head 22 forms a stepped bore 26, one end of which has the internal threads 20 and the other end has an annular lip 27. The bore 26 supports a one-way check valve 28 having an inlet end 29 positioned at one end of the bore 26. The check valve 28 can be of any type which can open in response to an increase in pressure at its inlet end 29 to admit gas and permit it to flow in one direction through the valve and which closes in response to pressure at its outlet end 30 when pressure at the inlet ends 29 is released to prevent gas flow in an opposite direction.

Figure 6:
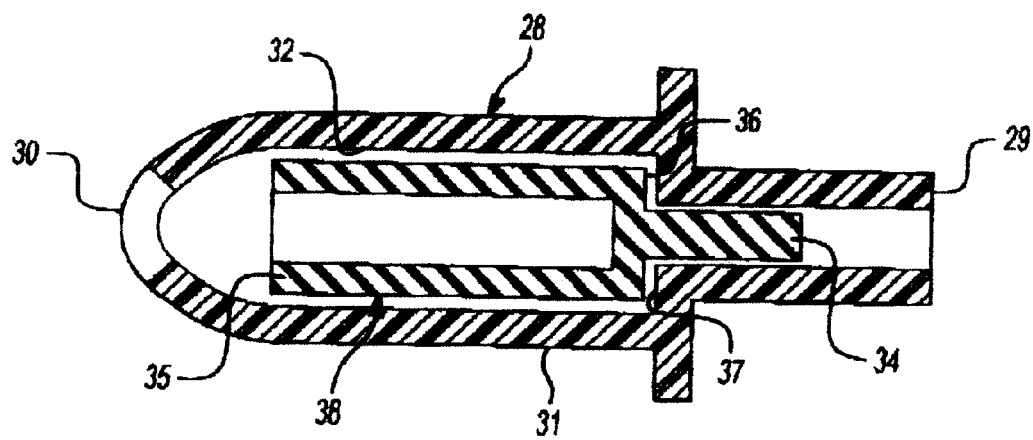
FIG. 6 is a view of the check valve used with the test apparatus seen in FIGS. 1 and 2.

One form of such check valve 28 is shown in FIG. 6 in which a tubular housing having an axial bore 32 holds a flexible, elastomeric valve closure element 33 having a guide stem 34 and a tubular portion 35 dispersed loosely in the bore 32. An annular surface 36 adjacent one end of guide stem 34 forms a closure to seat on annular sealing surface 37 in bore 32 to close the check valve 28 and prevent air flow in response to pressure at the outlet end 30. Upon application of air pressure at the inlet end 29, the valve closure element moves to the left as viewed in FIG. 6 to open the valve 28 to air flow from the inlet 29 to the outlet 30.

The tubular member 16 and head member 22 are threaded together to form an elongated test chamber 38, one end of which is closed by check valve 28 and the other end of which is closed by a screen 39. The chamber 36 serves to receive and hold a test strip 40. This type of strip is in the form of a material supported on a paper-like backing and has the characteristic of changing color when exposed to carbon monoxide or such other gases it may be desirable to detect. Such material is commercially available from American Chemical and Gas Company.

The housing 12 and particularly the tubular element 16 and head 22 are made of plastic material. The tubular element 16 can be made of transparent material or can be provided with a clear portion intermediate its two ends so that a strip 40 disposed in the chambers 36 can be viewed continuously.

A balloon 14 is mounted with its stem 15 stretched over the free end of the tubular element 16 and can be clamped in position on tubular element 16 by a band clamp 42. To place the apparatus 10 in condition for operation, the head 24 is temporarily unthreaded from tubular member 16 and a test strip 40 is placed in the chamber 36. After head 24 is unthreaded on tubular element 16, the apparatus 10 is ready for the testing procedure.

Testing procedures are conducted by holding the apparatus 10 with the inlet end 29 of check valve 28 and annular lip 27 flush against an outlet or air delivery port 44 of an air tank 46 or other source of air to be tested. When the control valve of its tank is opened to release air, the check valve 28 opens and air can pass through the bore 26 of the housing 12 and inflate the balloon 14. After the balloon 14 is inflated, the apparatus can be removed from the air delivery port 34 which causes the check valve 28 to close in response to the air pressure in the balloon and to hold the balloon in its inflated condition. At this time, the balloon 14 and chamber 38 contain a sample of the compressed air in the source of air 34. The test strip can be viewed through the walls of the transparent housing 16. If the test strip 40 changes color after a few minutes, carbon monoxide or other contaminant is present and the air is not suitable for breathing apparatus.

After the test sequence is completed, the test air is released and the balloon 14 is deflated by unthreading the head member 22 from tubular member 16. If the test strip has not reacted to the air sample the head 22 can be rethreaded on tubular element 16 and the test apparatus is ready to accept a test sample from still another container of compressed air. On the other hand, if the test strip has changed color, denoting air contamination, it must be removed and replaced before further testing can be continued.

Typically the test apparatus 10 can be made available in a package together with a few test strips and instructions for use.

The test apparatus is very portable and easily stored. It is easily moved from one source of air to another for convenient and rapid testing of multiple sources of compressed air without necessitating the use of additional tools to make connections.

Test apparatus for testing for the presence of carbon monoxide in air sources to be used for underwater breathing apparatus by divers has been provided which is compact and is easily transported and stored. Moreover, the apparatus is simple to use and produces accurate results economically and rapidly.

I claim:

1. Apparatus for testing the quality of air in a source of air under pressure, the combination comprising:
    a head member;
    a tubular member detachably connected to said head member and extending therefrom;
    said head member and tubular member forming a continuous, elongated bore;
    an inflatable member mounted on one end of said tubular member and being in fluid communication with said bore;
    a one-way check valve supported by said head member at one end of said bore and operable to admit air to said bore and prevent the escape of air from said bore; and
    a test strip disposed in said bore between said inflatable member and check valve, said inflatable member being inflated upon admission of air from a source of air to be tested through said check valve to said bore.

2. The apparatus of claim 1 wherein said tubular member is transparent to permit continuous viewing of the condition of said test strip.

3. The apparatus of claim 1 wherein said inflatable member is made of an elastomeric material.

4. The apparatus of claim 1 wherein said tubular member is connected to said head member by a threaded connection.

5. The apparatus of claim 1 wherein said head member and tubular member are detachable from each other.

6. The apparatus of claim 1 wherein said check valve has an annular inlet opening and said opening is disposed adjacent to a source of air to be tested to admit air.

7. Apparatus for testing a source of compressed air comprising;
    a housing having an elongated bore;
    an elastomeric bag detachably connected to said housing and communicating with one end of said bore;
    a one-way check valve disposed in said bore and communicating with the other end of said bore;
    said check valve being operable to admit air from a source of air to be tested to inflate said bag and maintain said bag is inflated;
    a test strip disposed in said bore between said bag and said check valve; and
    said housing having a transparent portion for viewing said test strip in said bore when said bag is inflated.

8. The apparatus of claim 7 wherein said housing member includes a tubular element and head element connected together by a detachable connection to form said bore.

9. The apparatus of claim 8 wherein said head element and tubular element are threaded together to form said detachable connection.

10. The apparatus of claim 8 wherein said tubular element forms said transparent portion of said housing.

11. The apparatus of claim 7 wherein said check valve is operable to open in response to air under pressure to admit air and inflate said bag.

12. The apparatus of claim 7 where said check valve is responsive in air in said bag when it is inflated to close said check valve.

13. The apparatus of claim 7 wherein a screen element is disposed at one end of said bore in said tubular element to permit passage of air in both directions between said tube and said bag.

14. The apparatus of claim 13 wherein said screen and said check valve form a chamber in said bore for containing said test strip.

* * * * *